US005900513A

United States Patent [19]
Ishida et al.

[11] Patent Number: 5,900,513
[45] Date of Patent: May 4, 1999

[54] PRODUCTION METHOD OF 2-CYCLOHEXENE-1-OL

[75] Inventors: Hiroshi Ishida, Kurashiki; Mitsuji Ono, Kojima-gun; Masazumi Chono, Kurashiki, all of Japan

[73] Assignee: Asahi Kasei Kogyo Kabushiki Kaisha, Osaka, Japan

[21] Appl. No.: 09/011,537

[22] PCT Filed: Sep. 12, 1996

[86] PCT No.: PCT/JP96/02615

§ 371 Date: Feb. 6, 1998

§ 102(e) Date: Feb. 6, 1998

[87] PCT Pub. No.: WO97/11045

PCT Pub. Date: Mar. 27, 1997

[30] Foreign Application Priority Data

Sep. 21, 1995 [JP] Japan ................................. 7-243103

[51] Int. Cl.⁶ .................................................. C07C 29/434
[52] U.S. Cl. .......................................... 568/825; 568/342
[58] Field of Search ...................................... 568/825, 342

[56] References Cited

U.S. PATENT DOCUMENTS

| | | | |
|---|---|---|---|
| 5,345,009 | 9/1994 | Sanderson et al. | 568/909.8 |
| 5,354,925 | 10/1994 | Sanderson et al. | 568/909.8 |
| 5,414,162 | 5/1995 | Sanderson et al. | 568/909.8 |

FOREIGN PATENT DOCUMENTS

| | | | |
|---|---|---|---|
| 41-2536 | 2/1966 | Japan | 568/825 |
| 43-8267 | 3/1968 | Japan | 568/825 |
| 49-93339 | 9/1994 | Japan | 568/825 |

*Primary Examiner*—James H. Reamer
*Attorney, Agent, or Firm*—Pennie & Edmonds LLP

[57] ABSTRACT

The present invention provide a method for producing 2-cyclohexene-1-ol which comprises using a catalyst containing an inetermetallic compound of palladium and lead and/or bismuth when cyclohexenyl hydroperoxide is subjected to hydrogenolysis to produce 2-cyclohexene-1-ol.

If the catalyst of the present invention is employed, it is possible to obtain the desired 2-cyclohexene-1-ol at a high selectivity with a much simpler reaction system than the prior art and, in addition, to inhibit the hydrogenation of coexisting cyclohexene sufficiently.

19 Claims, No Drawings

PRODUCTION METHOD OF 2-CYCLOHEXENE-1-OL

TECHNICAL FIELD

The present invention relates to a method for producing 2-cyclohexene-1-ol. More particularly, it concerns a method for producing 2-cyclohexene-1-ol using cyclohexenyl hydroperoxide as a starting material.

2-cyclohexene-1-ol is a precursor of 1,3-cyclohexadiene, which is suitable for making polymers, and a compound useful for various organic intermediates.

BACKGROUND ART

As a method for producing 2-cyclohexene-1-ol by hydrogenolysis of cyclohexenyl hydroperoxide, Japanese Patent Publication No. 2536/1966 reports a hydrogenolysis method using metallic palladium and a compound of lead or bismuth as a catalyst, which is carried out in the presence of a liquid hydrocarbon solvent, a hydrophilic solvent of lower alcohols and an organic base at about room temperature. As described below, however, the catalyst does not exhibit high activity by itself, and the activity of the catalyst is only 84% at maximum though improvement in the activity is attempted by adding a hydrophilic solvent and an organic base.

Incidentally, in Example 1 of the above reference, it is described that 2-cyclohexene-1-ol is obtained at a yield of 84% by hydrogenolysis of cyclohexenyl hydroperoxide with a metallic palladium/lead acetate catalyst using cyclohexene as a liquid hydrocarbon, ethanol as a hydrophilic solvent and quinoline as an organic base. On the other hand, Example 1–2 of the reference exemplifies the same reaction as Example 1 except that the organic base is not employed. The yield of 2-cyclohexene-1-ol is 63%.

In Example 5 of this patent publication, the reaction for obtaining 2-cyclohexene-1-ol is carried out by changing the amount of ethanol. As a result, too much reduction in the amount of ethanol causes the aggregation of the catalyst and deteriorates its activity. These disclosures show that it is essential to combine the hydrophilic solvent such as alcohol with the organic base in this method.

Further, the specification of this Japanese patent publication discloses that ethylenic hydrocarbon such as cyclohexene is inactive in a reduction reaction by hydrogen when used as a solvent. In the above Examples, however, the hydrogenation ratio of cyclohexene as a solvent is not disclosed.

Bull. Soc. Chim. France, 1964(6), P1302 contains an article of the inventors of Japanese Patent Publication No. 2536/1966.

Although the content of this article is almost the same as that of the Japanese patent publication, it further discloses that the hydrogenation ratio of cyclohexene is less than 1% when cyclohexene is employed as a solvent. However, a specific value of the hydrogenation ratio is not indicated.

Izvest. Akad. Nauk S.S.S.R., Otdel. Khim. Nauk 1958, P133 exemplifies a method for hydrogenolysis of cyclohexenyl hydroperoxide in an ethanol solvent using Raney nickel, platinum black and palladium black as a catalyst. However, the resultant product is only cyclohexanol having hydrogenated double bonds.

All the conventional methods have been carried out in the presence of a hydrophilic solvent such as alcohol, and preferable ones have been all carried out in the presence of a hydrophilic solvent and an organic base. Particularly, the methods wherein 2-cyclohexene-1-ol is obtained at a relatively high yield have been all carried out in the presence of an organic base such as quinoline using a catalyst comprising metallic palladium and lead or bismuth. However, the presence of plural components in the reaction system makes the separation of the product unduly complicated. Especially when 1,3-cyclohexadiene is produced by the dehydration reaction of the resultant 2-cyclohexene-1-ol using an acid catalyst, a special treatment such as rinsing is required since the acid catalyst is poisoned if the organic base remains even in a very small amount. Therefore, the use of organic bases is not industrially preferable.

DISCLOSURE OF THE INVENTION

The present inventors have made intensive and extensive studies to solve the above problems. As a result, they found that 2-cyclohexene-1-ol can be obtained at a high selectivity of 90% or more by using a catalyst containing an intermetallic compound of palladium and lead and/or bismuth, and accomplished the present invention.

Namely, the present invention relates to a method for producing 2-cyclohexene-1-ol which comprises using a catalyst containing an intermetallic compound of palladium and lead and/or bismuth when cyclohexenyl hydroperoxide is subjected to hydrogenolysis to produce 2-cyclohexene-1-ol.

According to the method of the present invention, the desired 2-cyclohexene-1-ol is obtained at a markedly high selectivity, which enables production on an industrial scale. In addition, the present method need not employ the organic base and the hydrophilic solvent such as alcohol, both of which have been conventionally used.

Hereinafter, the present invention is illustrated in more detail.

The catalyst of the present invention contains an intermetallic compound of palladium and lead and/or bismuth. As the intermetallic compound of palladium and lead, there are known ones having atomic ratios of palladium to lead of 1 to 1, 1 to 2, 2 to 1, 3 to 1, 3 to 2, 5 to 3 and the like. As the intermetallic compound of palladium and bismuth, there are known ones having atomic ratios of palladium to bismuth of 1 to 1, 1 to 2, 2 to 1, 3 to 1, 5 to 2 and the like. These intermetallic compounds can be identified by powder X-ray diffraction analysis using CuK α-rays. For example, the metallic palladium shows its diffraction peak at 2θ=39.80° to 40.2°. On the other hand, the intermetallic compound of palladium and lead in a ratio of 3 to 1 shows its peak at 2θ=38.550° to 38.70° which is ascribed to (111) face. The intermetallic compound of palladium and bismuth in a ratio of 3 to 1 shows its peaks at 2θ=38.10° to 38.45° and at 40.85° to 41.10° which are ascribed (400) face and (221) face, respectively.

Among these intermetallic compounds of palladium and lead and/or bismuth, the preferred are compounds comprising palladium and lead and/or bismuth in a ratio of 1 to 2, 2 to 1 and 3 to 1, and the most preferred is the one comprising palladium and lead and/or bismuth in a ratio of 3 to 1. In the case that both lead and bismuth atoms are contained, the atomic ratio indicates a ratio of palladium to the total of lead and bismuth.

The reason why the intermetallic compound shows high selectivity is not clearly known. It is considered that the conventional catalyst comprising metallic palladium and lead or bismuth and the intermetallic compound of the present invention have completely different chemical properties in view that they show greatly different selectivity when the organic base is not employed.

The intermetallic compound of the present invention may contain, as a hetero-element, mercury, thallium, tellurium, nickel, chromium, cobalt, indium, tantalum, copper, zinc, zirconium, hafnium, tungsten, manganese, silver, rhenium, antimony, tin, rhodium, ruthenium, iridium, platinum, gold, titanium, aluminum, boron, silicon and the like at a small amount in addition to palladium and lead and/or bismuth. In this case, these hetero-elements form either an interstitial compound by entering into crystal lattices of the intermetallic compound of palladium and lead and/or bismuth, or a substituted compound by substituting a part of a crystal latticed metal. In general, the amount of these hetero-elements may be in the range of 10% or less by weight, preferably 5% or less by weight, based on the amount of palladium.

Further, the catalyst of the present invention can contain at least one compound selected from an alkaline metallic compound and an alkaline earth metal. In this case, the amount of the alkaline metallic compound and alkaline earth metal is 0.1 to 50% by weight, preferably 0.5 to 40% by weight, more preferably 1 to 30% by weight, based on the amount of palladium.

The catalyst of the present invention may be either metal per se or one supported by a carrier. The preferred is a catalyst supported by a carrier.

When a carrier is employed, the carrier can be active carbon, silica, alumina, silica alumina, zeolite, magnesia, magnesium hydroxide, titania, calcium carbonate and the like. Among these carriers, silica, alumina and silica alumina are preferable. Silica and silica alumina are more preferable.

The amounts of palladium and lead and/or bismuth supported by the carrier are not particularly restricted. In general, the amounts of palladium and lead and/or bismuth are both 0.1 to 30% by weight, preferably 0.5 to 20% by weight, more preferably 1.0 to 15% by weight, based on the weight of the carrier.

In the present invention, the catalyst contains an intermetallic compound of palladium and lead and/or bismuth. The atomic ratio of palladium to lead and/or bismuth in the catalyst is not restricted by the atomic ratio of palladium to lead and/or bismuth in the intermetallic compound. If palladium exists in excess over lead and/or bismuth, 2-cyclohexene-1-ol is successively hydrogenated by free palladium having high hydrogenation activity of double bonds so that cyclohexanol is likely to generate as a by-product in a large amount. On the other hand, lead and/or bismuth can exist in excess over palladium. Generally, the atomic ratio of palladium to lead and/or bismuth in the catalyst is preferably 3/10 to 3/0.5, more preferably 3/6 to 3/0.6, most preferably 3/3 to 3/0.7.

The amount of catalyst used in the present invention is not particularly restricted. From the practical viewpoint, the catalyst is employed preferably in a weight ratio of 0.01 to 10 based on cyclohexenyl peroxide in the case of a batch method. The ratio is more preferably 0.05 to 1.0. In the case of a flowing method, weight hourly space velocity (WHSV) based on the cyclohexenyl peroxide is 0.01 to 100 $hr^{-1}$, preferably 0.1 to $10hr^{-1}$.

The palladium, lead and bismuth compounds to be used for the preparation of catalysts are suitably selected from, for instance, an organic acid salt such as a formate and an acetate, an inorganic acid salt such as a sulfate, a hydrochloride and a nitrate, an organic metallic complex such as an amine complex, a benzonitrile complex and a triphenyl complex, an oxide, a hydroxide and the like. The preferable palladium compounds are a palladium chloride, a palladium acetate and the like. The preferable lead compounds are a lead nitrate, a lead acetate and the like. The preferable bismuth compounds are a triphenyl bismuth and the like. The alkaline metallic compound and alkaline earth metallic compound are also selected from an organic acid salt, an inorganic acid salt, a hydroxide and the like.

The catalyst is prepared according to various methods. A typical method for preparing a supported catalyst comprises the steps of impregnating an appropriate carrier with a solution of soluble lead and/or bismuth, to which, if necessary, the above-mentioned compound comprising an alkaline metal and an alkaline earth metal are added; conducting evaporation for drying and solidification the resultant; impregnating the solid resultant with an acid solution of soluble palladium salt such as palladium chloride during heating; and reducing the impregnated product with a reducing agent such as hydrazine or hydrogen gas to produce a supported catalyst.

The supported catalyst can also be prepared according to another method comprising the steps of preparing an aqueous solution or organic solvent solution containing a palladium compound and lead and/or bismuth compound, or preparing a solution containing palladium and lead and/or bismuth which is produced by precipitating a complex compound containing palladium and lead and/or bismuth in an appropriate ratio and dissolving the complex in another solvent; if necessary, adding an alkaline metallic compound or an alkaline earth metallic compound to the solution; impregnating an appropriate carrier with the prepared solution; and reducing the impregnated catalyst according to a wet reduction method with a reducing agent such as formalin or a dry reduction method with hydrogen gas after drying.

In the present invention, the hydrogenolysis reaction of cyclohexenyl hydroperoxide does not always require a solvent. However, it is preferable to conduct the reaction in the presence of a solvent in view of the stability of cyclohexenyl hydroperoxide. As a solvent, hydrocarbon type solvents such as cyclohexene, conventional hydrophilic solvents such as alcohol, water and the like can be employed. Among these, cyclohexene and water are preferably employed. Cyclohexene is more preferable.

The concentration of cyclohexenyl hydroperoxide in the solution is 0.1 to 70% by weight, preferably 1 to 50% by weight, more preferably 2 to 40% by weight.

It is remarkably advantageous to employ cyclohexene as a solvent since the solution produced at the preparation of cyclohexenyl hydroperoxide by oxidization of cyclohexene is used as a raw material of hydrogenolysis as it is. In this case, however, the hydrogenation ratio of cyclohexene becomes problematic. This is because, cyclohexene separated from the produced solution after the hydrogenolysis is recycled in the oxidation step of the preparation of cyclohexenyl hydroperoxide, and cyclohexene and cyclohexane produced by the hydrogenation of cyclohexene cannot be separated according to usual distillation due to the small difference of their boiling points so that cyclohexene is accumulated in the production process. The catalyst of the present invention shows extremely low hydrogenation activity of cyclohexene. Although it depends on the conditions, the activity can be usually controlled at 0.3% or less. Therefore, the catalyst of the present invention is very advantageous in industry.

Since water is produced in the hydrogenolysis reaction of the present invention, it always exists in the reaction system. The prior art teaches that the catalyst undesirably aggregates and its activity is deteriorated probably owing to free water as the amount of the hydrophilic solvent such as alcohol is reduced. On the contrary, the catalyst of the present invention is never influenced by the presence of free water even in the situation that the hydrophilic solvent such as alcohol does not coexist with the free water. Surprisingly, it is found that the catalyst of the present invention shows high activity in the presence of free water rather than in the absence of it when cyclohexene is used as a solvent, and can inhibit the hydrogenation of double bonds.

Further, as another example of the present invention, a method using water as a solvent can be included. This method can employ, as a raw material, a solution prepared by extracting cyclohexenyl hydroperoxide with water from a cyclohexene solution containing cyclohexenyl hydroperoxide obtained by oxidizing cyclohexene.

The raw material of the present invention, i.e., cyclohexenyl hydroperoxide, sometimes contains 2-cyclohexene-1-ol and 2-cyclohexene-1-one produced as by-products of the oxidization step of cyclohexene. In the case of the present invention, however, cyclohexenyl hydroperoxide may be subjected to hydrogenolysis reaction without removing the above-mentioned by-products.

The reaction temperature of the present invention is 0° to 120° C., preferably 40° to 100° C., more preferably 50° to 90° C. Particularly, in view that the present reaction is an exothermic reaction and is applied to industrial practice, the preferable temperature is in the range of 50° to 90° C., in which heat is easily removed.

The hydrogen pressure of the present invention is 1 to 30 atmospheric pressure, preferably 2 to 20 atmospheric pressure, more preferably 4 to 15 atmospheric pressure. When the hydrogen pressure is 30 atmospheric pressure or more, the hydrogenation of double bonds is undesirably apt to occur.

In the reaction method of the present invention, the catalyst may be used in the form of a slurry or in a fixed bed. Further, the reaction can be carried out in either a batch style or a flow style.

BEST MODE FOR CARRYING OUT THE INVENTION

The present invention is illustrated in more detail referring to Examples below.

EXAMPLE 1

1.76 g of magnesium acetate was dissolved in 40 g of water, and 10 g of silica gel was added thereto. The resultant mixture was impregnated in a boiling water bath, evaporated to dry and solidify, and then calcined at 500° C. for 3 hours in air. To the calcined product was added a solution of diluted hydrochloride acid containing 0.83 g of palladium chloride and 0.92 g of lead acetate at 60° C. for impregnation. The impregnated product was filtered, dried and reduced at 300° C. in hydrogen flow for 3 hours. Then, the resultant product was washed with a solution of dilute sodium hydroxide and with water, and dried. When the resultant catalyst was subjected to X-ray diffraction analysis, the diffraction peaks were observed at $2\theta=38.6°$, $44.8°$, $65.4°$ and $78.6°$. It was confirmed that Pd and Pb of the catalyst formed an intermetallic compound of $Pd_3Pb_1$.

2.0 g of the above catalyst was added to 100 g of a cyclohexene solution containing 15% by weight of cyclohexenyl hydroperoxide, 1.3% by weight of 2-cyclohexene-1-ol and 1.3% by weight of 2-cyclohexene-1-one, and the resultant mixture was charged in a pressure vessel. Hydrogen was charged therein at 11 atmospheric pressure, and a hydrogenolysis reaction was carried out at 55° C. while being stirred. The result of the reaction is shown in Table 1.

EXAMPLE 2

0.5 g of the catalyst obtained in Example 1 was added to 100 g of a cyclohexene solution containing 12% by weight of cyclohexenyl hydroperoxide, 0.8% by weight of 2-cyclohexene-1-ol and 1.0% by weight of 2-cyclohexene-1-one, and the resultant mixture was charged in a pressure vessel. Hydrogen was charged therein at 11 atmospheric pressure, and a hydrogenolysis reaction was carried out at 70° C. while being stirred. The result of the reaction is shown in Table 1.

EXAMPLE 3

The hydrogenolysis reaction was carried out under the same conditions as in Example 2 except that 20 g of water was added. The result of the reaction is shown in Table 1.

Comparing the hydrogenolysis ratios in Examples 2 and 3, the reaction which employed water exhibited higher hydrogenolysis ratio. This means that water not only has no influence on the catalyst of the present invention but also accelerates the reaction.

EXAMPLE 4

1.76 g of magnesium acetate and 0.92 g of lead acetate were dissolved in 40 g of water, and 10 g of silica gel was added thereto. The resultant mixture was impregnated in a boiling water bath and evaporated to a dry solid while being stirred, and then calcined at 500° C. for 3 hours in air. To the calcined product was added a solution of diluted hydrochloride acid containing 0.83 g of palladium chloride, which was heated to 60°C., to impregnate the calcined product with palladium while being stirred. Next, after 2 cc of a formalin solution and a 1N sodium hydroxide solution were added, the resultant catalyst was filtered and dried. When the catalyst was subjected to X-ray diffraction analysis, it was confirmed that palladium and lead of the catalyst formed an intermetallic compound of $Pd_3Pb_1$ having diffraction peaks at $2\theta=38.6°$, $44.8°$, $65.4°$ and $78.60$.

0.5 g of the above catalyst was added to 100 g of a cyclohexene solution containing 2.0% by weight of cyclohexenyl hydroperoxide, 0.1% by weight of 2-cyclohexene-1-ol and 0.15% by weight of 2-cyclohexene-1-one, and the resultant mixture was charged in a pressure vessel. Hydrogen was charged therein at 6 atmospheric pressure, and a hydrogenolysis reaction was carried out at 50° C. with stirring. The result of the reaction is shown in Table 1.

EXAMPLE 5

A cyclohexene solution containing 20% by weight of cyclohexenyl hydroperoxide was contacted with water to prepare a solution containing 2.3% by weight of cyclohexenyl hydroperoxide, 0.05% by weight of 2-cyclohexene-1-ol and 0.05% by weight of 2-cyclohexene-1-one. The concentration of cyclohexene in the resultant solution was about 200 ppm. 0.5 g of the catalyst obtained in Example 4 was added to 100 g of this solution to carry out a hydrogenolysis reaction under 6 atmospheric pressure at 50° C. The result of the reaction is shown in Table 1.

EXAMPLE 6

5 g of the catalyst obtained in Example 4 was added to 100 g of a cyclohexene solution containing 12.0% by weight of cyclohexenyl hydroperoxide, 0.8% by weight of 2-cyclohexene-1-ol and 1.0% by weight of 2-cyclohexene-1-one to carry out a hydrogenolysis reaction under 11 atmospheric pressure at 30° C. The result of the reaction is shown in Table 1.

COMPARATIVE EXAMPLE 1

25 g of granular alumina was immersed in 25 g of a palladium chloride solution containing 5% by weight of palladium at room temperature for 62 hours and at 80° to 90° C. for 5 hours for the purpose of penetration. After filtration and drying steps, the penetrated alumina was treated with hydrogen at 80° to 90° C. for 1 hour. Then, it was immersed in a solution prepared by dissolving 5 g of lead acetate in 25 g of water for 2 hours and dried at room temperature after filtration.

When the resultant catalyst was subjected to X-ray diffraction analysis, a diffraction peak was not observed at around $2\theta=38.6°$ and the peak of metallic palladium was observed.

Using 0.5 g of this catalyst, a hydrogenolysis reaction was carried out under the same conditions as in Example 2. The result of the reaction is shown in Table 1.

Comparing with Example 2, it is seen that the catalyst of the present invention exhibits extremely high selectivity of 2-cyclohexene-1-ol and further inhibits the hydrogenation of cyclohexene.

COMPARATIVE EXAMPLE 2

Using 5 g of the catalyst of Comparative Example 1, a hydrogenolysis reaction was carried out according to the same procedure as in Example 2 except that the hydrogen pressure was 11 atmospheric pressure and the temperature was 30° C. The result of the reaction is shown in Table 1.

COMPARATIVE EXAMPLE 3

A hydrogenolysis reaction was carried out under the same conditions as in Example 2 except that 20 g of ethanol and 0.5 g of quinoline were added. The result of the reaction is shown in Table 1.

EXAMPLE 7

20 g of a 5% palladium/silica alumina powder catalyst was added to 75 g of 1-propanol and heated to 90° C. with stirring. Then, 42 g of 10% by weight of a triphenyl bismuth/1-propanol solution was added thereto, and further 18.8 g of hydrazine-1 hydrate was added to carry out 1 hour reduction. The resultant slurry was cooled down to room temperature and allowed to stand, and the supernatant liquid was removed by decantation. Then, the slurry was washed with 200 cc of 1-propanol twice and subsequently with 200 cc of water three times, dried in nitrogen atmosphere at 100° C. for 2 hours, and vacuum dried at 80° C. to obtain a palladium/bismuth catalyst.

When the resultant catalyst was subjected to powder X-ray diffraction analysis, the diffraction peaks were observed at $2\theta=38.840°$, $44.780°$, $65.780°$ and $78.660°$. When 5% palladium/silica alumina was analyzed as well as the catalyst, the diffraction peaks were observed at $2\theta=39.960°$, $46.44°$, $68.16°$ and $81.82°$. As for the diffraction peak of the resultant catalyst, $2\theta$ was shifted to the side of a lower angle as compared to that of metallic palladium. This indicates that palladium and bismuth formed an intermetallic compound.

Using this catalyst, a reaction was carried out under the same conditions as in EXAMPLE 1.

After the reaction period of 1.5 hours, the hydrogenolysis ratio of cyclohexenyl hydroperoxide reached 100%. The selectivities of 2-cyclohexene-1-ol, 2-cyclohexene-1-one, cyclohexanol and cyclohexanone were 82%, 11%, 4.0% and 3.0%, respectively. The hydrogenation ratio of cyclohexene was 0.8%.

INDUSTRIAL APPLICABILITY

As described above, if the catalyst of the present invention is employed, it is possible to obtain the desired 2-cyclohexene-1-ol at a high selectivity with a much simpler reaction system than the prior art and, in addition, to inhibit the hydrogenation of coexisting cyclohexene sufficiently.

TABLE 1

| Example & Comparative Example | Ex. 1 | Ex. 2 | Ex. 3 | Ex. 4 | Ex. 5 | Ex. 6 | Comp. Ex. 1 | Comp. Ex. 2 | Comp. Ex. 3 |
|---|---|---|---|---|---|---|---|---|---|
| Hydrogenolysis Ratio of Cyclohexenyl Hydroperoxide (%) | 100 | 100 | 100 | 100 | 100 | 100 | 100 | 100 | 100 |
| Selectivity (%) | | | | | | | | | |
| 2-cyclohexene-1-ol | 90 | 90 | 90.5 | 90 | 90.5 | 90.2 | 48 | 62 | 82 |
| 2-chylohexene-1-one | 7.9 | 8.1 | 8.3 | 7.8 | 7.3 | 7.0 | 18 | 10 | 11 |
| cyclohexanol | 1.1 | 1.2 | 0.7 | 1.0 | 1.1 | 1.2 | 18 | 16 | 4.0 |
| cyclohexanone | 1.0 | 0.7 | 0.5 | 1.2 | 1.1 | 1.6 | 16 | 12 | 3.0 |
| Hydrogenation Ratio of Cyclohexene (%) | 0.01 | 0.01 | 0.01 | 0.03 | Unable to analyze | 0.009 | 5.1 | 1.5 | 0.8 |
| Reaction Period (hr.) | 1.0 | 2.0 | 1.5 | 1.5 | 1.5 | 1.5 | 1.0 | 1.5 | 1.5 |

According to the reaction system employing alcohol and quinoline as disclosed in the prior art, the selectivity of 2-cyclohexene-1-ol is indeed relatively high, i.e., 80% or more, and the hydrogenation ratio of cyclohexene is 1% or less. However, this hydrogenation ratio is one digit larger than that of the present invention.

We claim:

1. A method for producing 2-cyclohexene-1-ol which comprises using a catalyst containing an intermetallic compound of palladium and lead and/or bismuth when cyclohexenyl hydroperoxide is subjected to hydrogenolysis to produce 2-cyclohexene-1-ol, wherein the hydrogenolysis is carried out in the presence of cyclohexene.

2. The method for producing 2-cylohexene-1-ol according to claim 1, wherein the intermetallic compound has an atomic ratio of palladium to lead and/or bismuth of 3 to 1.

3. The method for producing 2-cyclohexene-1-ol according to claim 1, wherein the catalyst contains an intermetallic compound of palladium and lead.

4. The method for producing 2-cyclohexene-1-ol according to claim 1, wherein the catalyst contains an intermetallic compound of palladium and bismuth.

5. The method for producing 2-cyclohexene-1-ol according to claim 1, wherein a concentration of said cyclohexenyl hydroperoxide is 0.1 to 70% by weight.

6. The method for producing 2-cyclohexene-1-ol according to claim 1, wherein a concentration of said cyclohexenyl hydroperoxide is 1 to 50% by weight.

7. The method for producing 2-cyclohexene-1-ol according to claim 1, wherein a concentration of said cyclohexenyl hydroperoxide is 2 to 40% by weight.

8. The method for producing 2-cyclohexene-1-ol according to claim 1, wherein said hydrogenolysis is carried out at a temperature between 0° and 120° C.

9. The method for producing 2-cyclohexene-1-ol according to claim 1, wherein said hydrogenolysis is carried out at a temperature between 40° and 100°° C.

10. The method for producing 2-cyclohexene-1-ol according to claim 1, wherein said hydrogenolysis is carried out at a temperature between 50° and 90° C.

11. The method for producing 2-cyclohexene-1-ol according to claim 1, wherein said hydrogenolysis is carried out at a hydrogen pressure between 1 and 30 atmospheric pressure.

12. The method for producing 2-cyclohexene-1-ol according to claim 1, wherein said hydrogenolysis is carried out at a hydrogen pressure between 2 and 20 atmospheric pressure.

13. The method for producing 2-cyclohexene-1-ol according to claim 1, wherein said hydrogenolysis is carried out at a hydrogen pressure between 4 and 15 atmospheric pressure.

14. The method for producing 2-cyclohexene-1-ol according to claim 1, wherein a concentration of said cyclohexenyl hydroperoxide is 0.1 to 70% by weight, said hydrogenolysis is carried out at a temperature between 0° and 120° C., and at a hydrogen pressure between 1 and 30 atmospheric pressure.

15. The method for producing 2-cyclohexene-1-ol according to claim 1, wherein a concentration of said cyclohexenyl hydroperoxide is 1 to 50% by weight, said hydrogenolysis is carried out at a temperature between 40° and 100°C., and at a hydrogen pressure between 2 and 20 atmospheric pressure.

16. The method for producing 2-cyclohexene-1-ol according to claim 1, wherein a concentration of said cyclohexenyl hydroperoxide is 2 to 40% by weight, said hydrogenolysis is carried out at a temperature between 50° and 90° C., and at a hydrogen pressure between 4 and 15 atmospheric pressure.

17. The method for producing 2-cyclohexene-1-ol according to claim 14, wherein the intermetallic compound has an atomic ratio of palladium to lead and/or bismuth of 3 to 1.

18. The method for producing 2-cyclohexene-1-ol according to claim 15, wherein the intermetallic compound has an atomic ratio of palladium to lead and/or bismuth of 3 to 1.

19. The method for producing 2-cyclohexene-1-ol according to claim 16, wherein the intermetallic compound has an atomic ratio of palladium to lead and/or bismuth of 3 to 1.

\* \* \* \* \*